(12) United States Patent
Haider et al.

(10) Patent No.: US 12,400,759 B1
(45) Date of Patent: Aug. 26, 2025

(54) ORTHOBIOLOGIC IMPLEMENTATION SYSTEM

(71) Applicant: Xenco Medical, LLC, San Diego, CA (US)

(72) Inventors: Jason Haider, San Diego, CA (US); Fred Murillo, San Diego, CA (US)

(73) Assignee: Xenco Medical, LLC, San Diego, CA (US)

( * ) Notice: Subject to any disclaimer, the term of this patent is extended or adjusted under 35 U.S.C. 154(b) by 0 days.

(21) Appl. No.: 19/035,180

(22) Filed: Jan. 23, 2025

Related U.S. Application Data

(63) Continuation of application No. 18/810,822, filed on Aug. 21, 2024.

(60) Provisional application No. 63/674,438, filed on Jul. 23, 2024.

(51) Int. Cl.
| | |
|---|---|
| *G16H 40/67* | (2018.01) |
| *A61B 5/00* | (2006.01) |
| *A61B 5/11* | (2006.01) |
| *A61L 27/12* | (2006.01) |
| *A63B 71/06* | (2006.01) |

(52) U.S. Cl.
CPC ........... *G16H 40/67* (2018.01); *A61B 5/0077* (2013.01); *A61B 5/1116* (2013.01); *A61B 5/1127* (2013.01); *A61B 5/7465* (2013.01); *A61L 27/12* (2013.01); *A63B 71/0622* (2013.01)

(58) Field of Classification Search
None
See application file for complete search history.

(56) References Cited

U.S. PATENT DOCUMENTS

| | | | |
|---|---|---|---|
| 10,532,000 B1* | 1/2020 | De Sapio | A63B 24/0062 |
| 2013/0117040 A1 | 5/2013 | James et al. | |
| 2014/0031895 A1 | 1/2014 | Rahimi et al. | |
| 2016/0024983 A1 | 1/2016 | Jones et al. | |
| 2017/0344726 A1 | 11/2017 | Duffy et al. | |
| 2018/0008440 A1 | 1/2018 | Khenansho | |
| 2018/0014891 A1* | 1/2018 | Krebs | A61B 5/055 |
| 2018/0154147 A1 | 6/2018 | Izvorski et al. | |
| 2019/0251340 A1 | 8/2019 | Brown et al. | |
| 2019/0295436 A1 | 9/2019 | Rubinstein et al. | |
| 2019/0295437 A1 | 9/2019 | Rubinstein et al. | |
| 2020/0051446 A1 | 2/2020 | Rubinstein et al. | |
| 2020/0188554 A1 | 6/2020 | Govil | |
| 2021/0264144 A1 | 8/2021 | Cho et al. | |
| 2021/0312236 A1* | 10/2021 | Goncharov | G06N 20/00 |
| 2021/0319894 A1* | 10/2021 | Sobol | G16H 20/30 |
| 2022/0183592 A1 | 6/2022 | Oliveira Santos et al. | |
| 2022/0299542 A1 | 9/2022 | Ramalho Ferreira et al. | |
| 2022/0328159 A1 | 10/2022 | Greenberg et al. | |
| 2023/0004236 A1 | 1/2023 | Branquinho Gomes et al. | |
| 2023/0022710 A1* | 1/2023 | Aubin | G06F 30/20 |
| 2023/0154091 A1 | 5/2023 | Cho et al. | |

(Continued)

*Primary Examiner* — Yi-Shan Yang
(74) *Attorney, Agent, or Firm* — Garrett H. Anderson

(57) ABSTRACT

Orthobiologics systems and methods for evaluation of exercise performance, such as physical rehabilitation performance, alone or in combination with pain remediation strategies are disclosed herein. The disclosure provides surgical inserts conducive to healing, approaches for monitoring and evaluation of surgical and nonsurgical rehabilitation, and pain management, collectively for the encouragement of rehabilitation from physical pain such as movement related physical pain.

25 Claims, 5 Drawing Sheets

(56) References Cited

U.S. PATENT DOCUMENTS

| | | | |
|---|---|---|---|
| 2024/0020409 A1* | 1/2024 | Kwok | G06N 3/08 |
| 2024/0095951 A1 | 3/2024 | Ramachandra et al. | |
| 2024/0260892 A1* | 8/2024 | Haas | A61B 5/4824 |
| 2024/0393808 A1* | 11/2024 | Akaike | G05D 1/6987 |

* cited by examiner

ORTHOBIOLOGIC IMPLEMENTATION SYSTEM

CROSS-REFERENCE TO RELATED APPLICATIONS

This document claims priority to U.S. Prov Ser. No. 63/674,438, filed Jul. 23, 2024, and further claims priority to U.S. application Ser. No. 18/810,822, filed Aug. 21, 2024, the contents of each of which are hereby incorporated by reference in their entirety.

BACKGROUND

Orthobiologics have sweeping surgical applications in treating general orthopedic and spinal pathologies. Though orthobiologics have been widely accepted as treatment for a wide number of general orthopedic and spinal pathologies, the scope of their intervention has been limited to the surgical or clinical setting. A significant gap has remained in the monitoring and amplification of these orthobiologics during the post-operative recovery phase of patients.

Orthobiotics have been produced, for example the Signafuse by Bioventus Surgical and the Vitoss spine product by Stryker. However, these products are not integrated into a rehabilitation or therapy regime so as to facilitate at home rehabilitation compliance through ready feedback, recommendations and pain management.

Similarly, pain management and exercise body monitoring have been developed, for example by Hinge Health, Sword Health, Omada Health, Kaia Health, Bardavon, Dario Health and Dorsa VI.

However, to date, there have been no digitally-enabled orthobiologic technologies that enable treating physicians to link the implantation or injection of an orthobiologic to mobility changes and physical therapy adherence, to direct patient rehab course selection or to monitor rehab adherence or efficacy, or to supplement or address challenges associated with pain management, particularly the risk of addiction associated with pharmaceutical pain management.

There is an unmet but critical need for continuity between the intraoperative or clinical treatment phases of a patient's journey and the recovery phases which is underscored by the scientifically-validated link between surgical success and physical therapy.

Additionally, though orthobiologics have been proven to be effective in pain management as both injectables and implants, there has been an unmet need to directly compound their efficacy with software-driven pain management technologies anchored in art therapy.

SUMMARY

Disclosed herein are orthobiologic kits, such as kits comprising one or more of an implantable orthobiologic, a pose estimation software package, a pain alleviation suite, and a physician portal software package. In some such kits, the implantable orthobiologic comprises a tag. Some implantable orthobiologics comprise one or more of bioactive glass, beta-tricalcium phosphate such as in granule form, hydroxyapatite in some cases in common granules with the beta-tricalcium phosphate, and collagen, such as bovine collagen. The implantable orthobiologic in some cases mimics kit recipient or user bone, and may be consistent with healing achieved through use of a patient autologous bone graft.

Kits often comprise at least one sticker corresponding to the tag, such that a user may be labeled according to the biologic used. Some kits comprise hermetically sealed packaging having an identification code corresponding to the tag. The tag is in some cases scannable.

The pose estimation package is often configured to interface or interfaces with one or more of a mobile image capture device, positional markers on a user, or a wearable motion sensor. The pose estimation package in some cases comprises a wearable motion sensor. Alternately, the pose estimation package in some cases identifies user posture and motion without relying upon exogenous markers, in these cases identifying for example user landmarks such as joints and using these to analyze user movement data.

The user is in some cases a surgical recipient of the implantable orthobiologic. The pose estimation package in some cases comprises a kinetic model for at least one rehabilitation exercise. The pose estimation package in some cases identifies at least one anatomical landmark in a user motion dataset. The user motion dataset may comprise at least one video frame or at least one position monitor data array, and in some cases the pose estimation package identifies the at least one anatomical landmark using a deep learning model.

In some kits, the deep learning model comprises a machine learning library, such as one comprising a Pytorch learning library. The deep learning model is in some cases validated against at least one annotated reference dataset.

The pose estimation package in some cases evaluates positional information deviation from at least one annotated reference dataset and may display an image comprising the at least one anatomical landmark, record completion of an exercise, and may display completion of the exercise.

The pain alleviation suite receives a first user pain rating, which may be user self-reported. The first user pain rating may be provided prior to the pain alleviation suite generating an output, and may be informed at least in part by an assessment of deviation of user positional information deviation from at least one annotated reference dataset. Some pain alleviation suites recommend a pain treatment, such as a pain treatment comprising mental engagement, such as, generative art creation software, puzzle engagement, music or other metal activity to direct attention away from a pain source. The generative art creation software in some cases provides a colorable art template, or a visual puzzle.

The pain treatment in some cases comprises a pain medication, alone or in combination with the generative art. The pain treatment is often proposed to an observing medical professional.

The pain alleviation suite in some cases receives a second user pain rating subsequent to the pain treatment. In some of these cases, the pain alleviation suite assesses effectiveness of the pain treatment, such as in light of the second user pain rating.

The physician portal software package often monitors a user's pain score over time. Additionally or in the alternative, the physician portal software package monitors one or more of a user's change in positional information deviation from at least one annotated reference dataset over time, or a user's physical therapy schedule adherence over time. The physician portal software package in some cases displays a user pain treatment recommendation. So as to facilitate remote monitoring the physician portal software package is accessible through the internet, or on a mobile internet device. The physician portal software package often allows physician user communication.

Some kits comprise a community interface package, such as one that facilitates performance data exchange between a first user and a second user.

Disclosed herein are methods of encouraging compliance to a recovery regimen, some such methods comprising one or more of digitally monitoring a user first physical therapy performance, digitally assessing divergence in user first physical therapy performance from a first physical therapy performance model performance, receiving a user first pain assessment, providing a user art based pain management exercise, and receiving a user second pain assessment.

The recovery regimen is variously an orthobiologic intervention, a surgical intervention or a physical therapy intervention. Digitally monitoring comprises video recording, and may comprise recording user position monitoring marker location.

Digitally assessing in some cases comprises applying a deep learning model, such as one comprising using a machine learning library, such as a machine learning library that corresponds to a position monitoring output associated with an implantable orthobiologic delivered to the user.

A number of mental activity or art based pain management approaches are consistent with the disclosure herein, such as drawing or puzzle solving. Alternate mental activity approaches such as word association, vocabulary puzzle or similar approaches that distract or focus a user's attention away from physical pain are also consistent with the disclosure herein. Such activities decrease user pain while reducing the risk pain medication addiction associated with recovery.

Some aspects of the methods herein comprise comparing the divergence or difference in user first physical therapy performance to the user first pain assessment, alternately or in combination comprising comparing the divergence in user first physical therapy performance to the user second pain assessment, alternately or in combination comprising reporting at least one of the divergence in user first physical therapy performance, first user pain assessment and second user pain assessment to the user.

Reporting variously comprises indicating a value for at least one previous physical performance of at least one of the divergence in user previous physical therapy performance, previous first user pain assessment and previous second user pain assessment to the user or to a third party directing the user. Similarly, in some cases reporting comprises indicating a value for at least five previous physical performances of at least one of the divergence in user previous physical therapy performance, previous first user pain assessment and previous second user pain assessment to the user. The report may comprise an indication of improvement for at least one previous physical performance of at least one of the divergence in user previous physical therapy performance, previous first user pain assessment and previous second user pain assessment to the user.

Some methods comprise reporting at least one of the divergence in user first physical therapy performance, first user pain assessment and second user pain assessment to a medical practitioner such as a medical practitioner is remote to the user. Alternately or in combination, some methods comprise reporting at least one of the divergence in user first physical therapy performance, first user pain assessment and second user pain assessment to a user community.

Also disclosed herein are methods comprising providing a movement exercise to a user, generating a record of the user performing the movement exercise, and assessing divergence between the recording and a reference performance of the movement exercise. Some such methods comprise one or more of reporting divergence between the recording and a reference performance of the movement exercise to the user, or reporting divergence between the recording and a reference performance of the movement exercise to a medical practitioner, such as a medical practitioner remote to the user. The movement exercise variously comprises a rehabilitation exercise, such as one targeted to prevent surgical intervention, or to facilitate recovery from surgical intervention, such as an intervention comprising introduction of an orthobiologic to the user. In some cases the intervention is targeted to prevention of harm to the user.

Movement exercises variously comprise an athletic training exercise.

Assessing divergence or difference may comprise one or more of performing a computational analysis of the user performing the movement exercise, such as a computational analysis comprising artificial intelligence analysis of the user performing the movement exercise, for example so as to identify one or more of a user body part or parts responsible for the divergence, or user joints responsible for the divergence, or user movement subcomponents responsible for the divergence.

A reference is in some cases a healthy performance of the movement exercise, or a prior user performance of the movement exercise.

Some aspects of the methods comprise receiving one or more of a self reported pain level from the user prior to performing the movement exercise, or a self reported pain level from the user subsequent to performing the movement exercise.

Some aspects of the methods comprise providing to the user a nonmedicinal pain management exercise subsequent to the user performing the movement exercise, such as one or more of immediately subsequent to the user performing the movement exercise.

Some aspects of the methods comprise receiving a self reported pain level from the user subsequent to performing the nonmedicinal pain management exercise, or prior to performing the movement exercise, receiving a self reported pain level from the user subsequent to performing the movement exercise, providing to the user a nonmedicinal pain management exercise subsequent to the user performing the movement exercise, and comprising receiving a self reported pain level from the user subsequent to performing the nonmedicinal pain management exercise.

Various embodiments of the method comprise generating a report of the assessing, such as generating a report of the assessing and of the patient self reported pain levels from at least one of prior to performing the movement exercise, subsequent to performing the movement exercise and subsequent to performing the nonmedicinal pain management exercise.

A report variously comprises an assessment of whether the user performance constitutes a substantial match to the reference, such as a substantial match comprising at least 80% match to the reference performing.

A report variously comprises one or more of assessment of a degree of divergence from the reference, or extent of compliance to a temporal regimen of movement performance exercises.

The report is provided variously to one or both of the user or to a medical practitioner, such as a medical practitioner remote to the user.

The method often comprising assessing contents of the report to select a progression course through a movement exercise regimen, such as by selecting a next movement exercise when user performance constitutes a substantial match to the reference. The next movement exercise may be selected from a linear exercise regimen, such as may be provided by a medical practitioner.

In some cases assessing contents of the report to select a progression course through a movement exercise regimen comprises selecting a next movement exercise when user performance constitutes a substantial match to the reference. In some cases assessing contents of the report to select a progression course through a movement exercise regimen comprises selecting a next movement exercise to target a user joint when user performance differs from the reference related to movement at the user joint. Similarly, assessing contents of the report to select a progression course through a movement exercise regimen may comprise selecting a next movement exercise when at least one user self reported pain level is below a threshold.

Some methods comprise reporting results of the assessing to a medical practitioner such as a medical practitioner is remote to the user.

Also disclosed herein are methods of encouraging compliance to a movement regimen. Some such methods comprise one or more of providing a nonmedicinal pain management exercise to a user immediately subsequent to user performance of a movement exercise of the exercise regimen, providing a performance assessment to the user immediately subsequent to user performance of a movement exercise of the exercise regimen, and providing the performance assessment to a medical practitioner, such as a medical practitioner remote to the user.

The user in some cases exhibits improved compliance as indicated by one or more of the following: compliance corresponding to adherence to the exercise regimen better than at least 50% of users provided the exercise regimen without being provided the nonmedicinal pain management exercise immediately subsequent to performance; compliance corresponding to adherence to the exercise regimen better than at least 50% of users provided the exercise regimen without being provided the performance assessment immediately subsequent to performance; compliance corresponding to adherence to the exercise regimen better than at least 50% of users provided the exercise regimen without providing the performance assessment to a medical practitioner.

Also disclosed herein are methods of selecting a physical mobility intervention course, such as methods comprising one or more of digitally monitoring a user first physical performance, digitally assessing divergence in user first physical performance from a first physical performance model performance, receiving a user first pain assessment, and selecting an implantable orthobiologic to introduce into the first user. Digitally monitoring variously comprises one or more of video recording, recording user position monitoring marker location, applying a deep learning model such as one using a machine learning library, for example a machine learning library corresponding to at least one position monitoring output associated with a defect addressable using an implantable orthobiologic delivered to the user.

Selecting an implantable orthobiologic variously comprises one or more of weighing user first pain assessment and divergence in user first physical performance from a first physical performance model performance; identifying an implantable orthobiologic to address the defect; or assessing user first pain assessment.

Consistent with the above, disclosed herein are kits for practice of any of the methods disclosed above or elsewhere herein.

Consistent with the above, disclosed herein are kits comprising a pose estimation software package, a pain alleviation suite, and a physician portal software package. Some such kits comprise one or more of a wearable sensor, or an implantable orthobiologic.

Also disclosed herein consistent with the methods and kits above are implantable orthobiologics, such as those comprising one or more of a porous biocompatible matrix, and a population of composite granules. The matrix often comprises a biocompatible flexible material capable of maintaining pores, such as collagen, for example bovine collagen, xenically expressed human collagen, such as from a bacterial or yeast expression system, harvest user collagen, or collagen mimic material. The matrix often comprises a sold structural component, such as dispersed bioactive glass particles. The matrix maintains a porosity, such as one that exhibits a porosity interconnectivity of at least 70%. The matrix maintains a porosity, such as one that exhibits a porosity interconnectivity of at least 80%. The matrix maintains a porosity, such as one that exhibits a porosity interconnectivity of 80%-90%.

Often, the matrix comprises pores of at least 350 um diameter, such as pores of a diameter ranging from 500 um to 600 um, or pores of a diameter ranging from 530 um to 570 um or other sizes consistent with the disclosure herein.

The granules are often embedded in the matrix, in some case so as to convey structural integrity to the matrix. The granules often exhibit a higher density than the matrix. Granules are often heterogeneous, and may comprise one or more of a resorption component and a structural component. The resorption component variously comprises at least 50% of the granule for each granule, or at least 60%, at least 70%, at least 80%, or at least 90% of the granule for each granule. In some cases the resorption component comprises about 95% of the granule for each granule. The resorption component in some cases comprises beta-tricalcium phosphate.

The structural component variously comprises no more than 50% of the granule for each granule, or no more than 40%, 30%, 20%, 10%, or comprises no more than 5% of the granule for each granule, such as about 5% of the granule for each granule. The structural component in some cases comprises hydroxyapatite.

The orthobiologic often comprises an imbibed cell population, such as an imbibed cell population introduced into the matrix. The imbibed cell population may comprise mesenchymal cells. The imbibed cell population may comprise cells from a bone marrow aspirate. The cells are in some cases autologous, or autochthonous. Cells are in some cases harvested from the user prior to insertion of the orthobiologic into the user.

Similarly, some methods comprise harvesting user cells such as mesenchymal cells, bone stem cells, or bone marrow aspirate cells, and infusing said cells into an orthobiologic as disclosed herein or otherwise known in the art, and introduction of the orthobiologic into a user. The orthobiologic is in some cases uniquely or recognizably labeled such that it may be correlated to a treatment regimen or a performance record or performance data set corresponding to user performance.

Also disclosed herein are orthobiologics and kits consistent with the methods herein, and methods comprising use of orthobiologics disclosed herein pursuant to practice of the methods herein. Also disclosed herein are software and kits consistent with the methods herein, and methods comprising use of software to practice the disclosure herein pursuant to practice of the methods herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
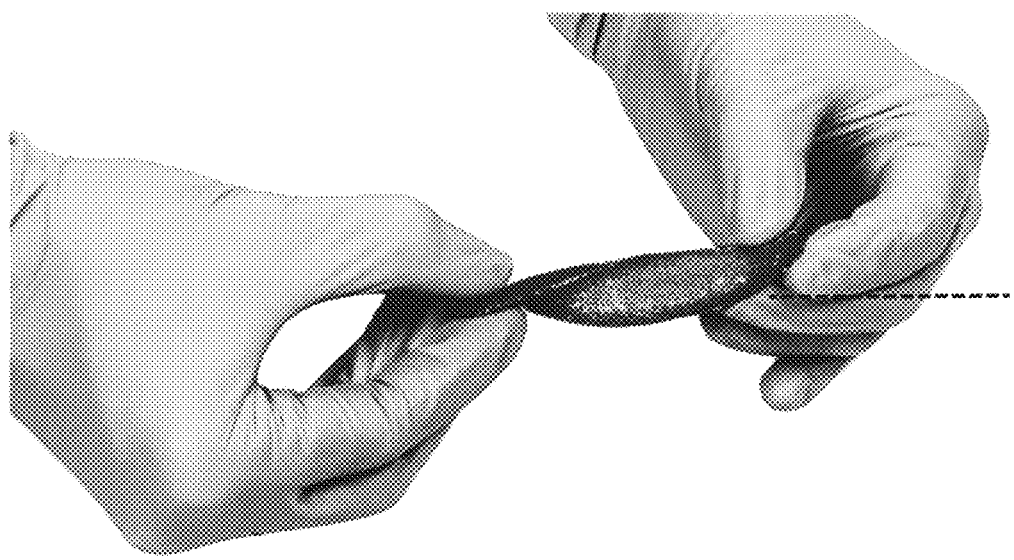
FIG. 1 shows an orthobiologic material withstanding stress of being twisted.

Disclosed herein are compositions systems and methods for user mobility assessment, such as may be used in combination with any one or more of orthobiologic surgical intervention, surgical or surgical alternative assessment, or traditional or alternative pain management. Some such systems comprise digitally-enabled orthobiologics platforms that feature one or more of a mobile application, Artificial Intelligence-driven software, a desktop-based portal, and an implanted or injected orthobiologic linked to the patient rehabilitation software through a unique or other activation code, and which may select or provide traditional or alternative pain recommendations.

Systems and methods are discussed herein in distinct sections, but it is understood that systems are contemplated as being used to perform methods disclosed herein as well as other methods, while methods disclosed herein may comprise use of disclosed systems or other compatible systems. Accordingly, it is understood that disclosure from either section may be understood in the context not only of that section but of the disclosure generally.

Orthobiologic and Other Systems for Physical Therapy

In cases comprising orthobiologic or other surgical intervention, after implantation or injection of the orthobiologic or performance of the surgical procedure, a treating or other healthcare provider can enroll the patient or user into a digital recovery platform using the unique identification code associated with the particular orthobiologic or procedure. Alternately a user may self-enroll or be enrolled by other third party. Once enrolled, the recovery profile of the treated patient or user is populated with the lot number and the biochemical characteristics of the orthobiologic used, or features of the intervention. Alternately, such as in cases of surgical selection or surgical alternative selection, or other use of the technology disclosed herein, the user or a medical practitioner, for example, may enter details of a diagnosis or other identifier into the digital platform.

The digital platforms disclosed herein are often customizable to each or a particular patient or user. Accordingly, unique physical therapy and pain management plans can be prescribed and monitored by a treating healthcare provider and correlated or directed to a patient or user. The primary method of delivery to a patient or user is through a mobile application that leverages the patient's on-device camera to track their kinematic motion and assess whether the prescribed physical therapy exercises have been sufficiently completed.

Additionally, the mobile application in some cases allows a patient or user to engage in alternate pain therapy such as art therapy for pain management, for example using AI-generated artwork for on-device coloring or puzzle completion, as well as in some cases having the ability to select accompanying sounds from a library of pre-installed or accessed recordings. The patient or user is in some cases prompted to enter their pain score before, after, or before and after each art therapy session. In various embodiments, a treating healthcare provider can use the desktop-based portal to monitor the patient's or user's physical therapy adherence and pain score progress as well as examine granular data on exercise repetitions and the effectiveness of specific art therapy sessions. Working in concert to inform the future treatment plans of the patient by the healthcare provider, one or more of the combined orthobiologic data, AI-enabled physical therapy analysis, and AI-generated art therapy pain management progress are interpolated by the technology to create a unique bio-digital patient recovery profile.

Through some embodiments of the mobile application, the patient is able to send and receive one or more of asynchronous text, image-based, and video messages to the healthcare provider or to additional users in an open or closed user community. A user is in some cases able to schedule a rehabilitation session, art session, or art session and rehabilitation session so as to complete said session or sessions in concert with fellow users, either in physical proximity or remove from one another, using interfaces provided by the application. Concurrent scheduling in some cases comprises sending an invitation to an individual or group, and upon acceptance of the invitation, establishing a joint session either in physical proximity or through an interface to facilitate one or more of remote communication and result sharing. Concurrent session performance in some cases increases the chance or frequency of session completion by at least, at most, about or exactly 10%, 20%, 30%, 40%, 50%, 75%, 100% or more.

Additionally, the desktop-based portal allows the healthcare provider to continuously enter additional patient data derived from external sources such as, for example, one or more of comorbidity and body mass index data as well as self-reported assessments of the patient's diagnostic imaging taken during the course of recovery.

Compositions, systems and methods disclosed herein are further understood in light of the following discussion of particular system component, which may in some cases correspond to or enable particular method steps.

Orthobiologic Component: An implantable or injectable orthobiologic is a component of some systems and methods herein, such as for bone regeneration in the spine, skeletal extremities, the pelvis, or any bone suffering from traumatic injury. Orthobiologics may be engineered from a broad range of biocompatible or bioactive components, such as bioactive glass, beta-tricalcium phosphate, hydroxyapatite, and collagen such as animal sourced collage such as bovine collagen or expressed transgenic collagen as may be produced from a bacterial or microbial system.

Orthobiologics include varieties with osteogenic, osteoinductive, and osteoconductive capabilities. These varieties include allografts, xenografts, and wholly synthetic biomaterials. Allografts can be defined as bone transplanted from a donor to a patient and are typically harvested from either a cadaver or a living donor. Xenografts can be defined as animal-derived bone with similar properties to allograft. Synthetic biomaterials are engineered, bone-mimicking or osteogenic materials that include ceramics, biopolymers, and peptides. Allografts, Xenografts, and the majority of synthetic biomaterials are delivered intraoperatively with certain injectable orthobiologics delivered in a clinical setting.

In exemplary embodiments, an orthobiologic mimics the patient's own bone to allow for healing in defects without the need to harvest from another site in the body. Alternate orthobiologics are autologous or comprise material drawn from a patient's body, or are autochthonous or drawn from a third party individual or entity.

Features common to many orthobiologics include being formed from a porous matrix. Porosity in some cases allows user cell invasion prior to, or subsequent to, or both prior to and subsequent to surgical implantation. Matrix porosity is often of pore sizes comparable to or greater than user cells in the vicinity of the orthobiologic insertion site.

Exemplary orthobiologics exhibit an interconnected porosity of about, at least or at most 50%, 60%, 70%, 75%, 80%, 85%, 90%, or 95%, or a range spanning values listed therein. Exemplary embodiments exhibit an interconnected porosity ranging from about or exactly 50% to 95%, 60% to 95%, 70% to 95%, 80% to 90%, 83% to 87%, about 85% or 85%.

A broad range of pore sizes are consistent with the disclosure herein. Pore sizes are in some cases selected to facilitate uptake of imbibed cells such as imbibed mesenchymal stem cells. Similarly, pores are also selected to facilitate nutrient and oxygen transport to the osteoblasts after attachment.

Pores consistent with the disclosure herein exhibit a mean or median diameter of about, at least or at most 100 um, 150 um, 200 um, 250 um, 300 um, 350 um, 400 um, 450 um, 500 um, 550 um, 600 um, 650 um, 700 um, 750 um, 800 um, 850 um, or 900 um, or a range spanning values listed therein. Exemplary embodiments exhibit a mean or median pore size ranging from 350 um-750 um, 400 um-700 um, 450-650 um, 500 um-600 um, 530 um-570 um, 540-560 um, about 550 um to 550 um.

So as to facilitate cell invasion, some orthobiologics are imbibed with user or third party cells to encourage cell invasion of the orthobiologic. A suitable cell population for such pre-surgical cell invasion is mesenchymal cells, or cells as may be obtained from a bone marrow aspirate, or other cells conducive to invasion of the orthobiologic matrix.

A broad range of biocompatible compositions are suitable matrix constituents. Exemplary matrices comprise collagen, though other biocompatible structural components compatible with porous matrix formation, cell invasion and resilient to the stress of introduction into a user are also contemplated. Some discussion of collagen and biomaterial scaffold formation is found in Drury and Mooney (2003) "Hydrogels for tissue engineering: scaffold design variables and applications" Biomaterials 24:4337-4351, which is hereby incorporated by reference in its entirety.

Matrices are in some cases supplemented using granules. Addition of granules to a matrix facilitates structural integrity, so as to allow larger or more frequent pores without surrendering structural integrity. Granule embedded matrices allow imbibing of a greater proportion of mesenchymal stem cells or other cells, and is conducive to imbibed cell survival due to maintaining structural integrity. Similarly, granule embedded matrices facilitate dispersion of stability factors such as bioactive glass through the matrix.

A broad range of granules are consistent with the disclosure herein. Granules denser than the matrix in which they are embedded are preferred in many embodiments, such as denser than collagen or denser than collagen and bioactive glass. Exemplary granules are selected to exhibit a high resorption rate, such that they are in some cases gradually broken down and released into the circulatory system. Alternately or in combination, exemplary granules are selected to exhibit a high structural stability prior to resorption, so as to allow long term stability of the orthobiologic and facilitating its replacement with native user tissue such as native user collage as may be involved in supplementation of replacement of the orthobiologic with native user bone or other tissue.

Accordingly, granules variously convey a structural functionality and a resorption functionality, either in a single composition or as a mixture of constituents. Some exemplary granule compositions comprise a high resorption constituent such as beta-tricalcium phosphate and a structural constituent such as hydroxyapatite. Various proportions of these high resorption constituents and structural constituents are consistent with the disclosure herein, such as 50%/50%, 60%/40%, 70%/30%, 80%/20%, 90%/10%, 95%/5%, 99%/1% or other proportions within or outside of the range of proportions presented herein. Some exemplary granules comprise 95% beta-tricalcium phosphate and 5% hydroxyapatite.

Similarly, some granules comprise beta-tricalcium phosphate and hydroxyapatite in molar proportions about, at least, at most or exactly 1:1, 2:1, 5:1, 10:1, 20:1, 30:1, 40:1, 50:1, 55:1, 60:1, 61:1, 62:1, 63:1, 64:1, 65:1, or 70:1, or a proportion spanned by our outside of the range of the ratios given herein.

Proportions as those listed herein convey particular benefits over the art. For example, prior art granules exhibiting a ratio of less than 1:1 (that is proportionally more hydroxyapatite than resorption agent) do not facilitate resorption or granule replacement by user cells, bone or collagen. Similarly, prior art granules having resorption components but lacking structural components often suffer from structural defects such that they may lose structural integrity pursuant to imbibing with cells or subsequent to introduction to a user.

An implant is in some cases delivered in hermetically-sealed packaging with a unique or distinguishing identification code, which may be printed on the package and on one or more, such as 6, removable stickers. Alternately, or in combination an implant may harbor an internal or removable chip that may provide or broadcast the identifying code.

Subsequent to unsealing an implant or orthobiologic, the orthobiologic is in some cases imbibed with cells, mesenchymal stem cells, for example from bone marrow aspirate. As mentioned above, the orthobiologics as disclosed herein exhibit greater structural stability, facilitating greater porosity and greater cell recruitment subsequent to imbibing. These improved features arise in part from the introduction of granules such as granules, for example those comprising 95% beta-tricalcium phosphate and 5% hydroxyapatite, and bioactivated glass. Consequently, orthobiologic compositions herein exhibit in some case a cell recruitment rate of at least, at most, about or exactly 10%, 20%, 30%, 40%, 50%, 75%, 100% or more greater than orthobiologics in the art.

The packaging is designed to allow a physician's team to either scan or physically remove one of the corresponding stickers to facilitate the subsequent enrollment of the patient into the a system herein, such as a digital physical rehabilitation and art therapy platform. When the sticker is scanned using a mobile application, or an identifier is otherwise inputted, the physician is prompted to enter one or more of the patient's or user's healthcare details and email address. The patient may be sent a direct link to download the corresponding, patient-facing mobile application. Once the patient downloads the app using the email invitation, their physical rehabilitation and art therapy progress will be viewable by their own healthcare provider. The unique or identifying ID creates a direct link between the specific implant that was used and the subsequent digital recovery journey.

Pose-Estimation Software Component: Some systems comprise pose-estimation software. Some such software that leverages the depth-sensing camera on a user's mobile device to capture and compare a video feed, for example of the real-time movement data of a patient during a physical rehabilitation session with kinematic models for each of the pre-loaded exercises. Alternately or in combination, some pose estimation software incorporates or collects positional marker data such as that generated from positional markers attached to a patient or user.

The pose-estimation software in some cases automatically undergoes preprocessing to filter noise before the software applies computer vision algorithms to analyze the video frames of the patient, such as in real time, to assess user or patient pose. Pose estimation in some cases comprises identification of key anatomical landmarks such as joints.

Some such software operates using an a priori algorithm, while alternatives are trained on datasets, such as large annotated datasets. Exemplary software embodiments detect a patient's joints through the use of deep learning models developed using a deep learning library such as the Pytorch machine learning library.

One exemplary deep learning model consistent with the disclosure is a Convolutional Neural Network. Exemplary Convolution Neural Networks comprise one or more of the following steps, which may also be adopted by alternate deep learning or AI models. The Network applies a filter to the visual exercise data obtained from the patient and produces a feature map that highlights regions of the input that match the filter's pattern.

The Convolutional Neural Network employs several layers of increasing specificity to identify the patient's joint positions. The first layer is the input layer, which is the raw sequence of video frames from the patient's exercise recording that undergoes instant preprocessing for performance. The next layer is the convolutional layer which extracts low-level features such as edges and textures. The following layer is the pooling layer, which reduces spatial dimensions for computational efficiency while retaining essential image information. The subsequent layer is the heatmap layer, which is a probability-driven output that features a set of heatmaps, one for each joint. The highest intensity points in these heatmaps correspond to the predicted joint locations. This heatmap is a two-dimensional representation where the intensity at each pixel indicates the probability of a patient's joint being located at that position. The final step in the Convolutional Neural Network is post-processing, which identifies the peaks in heatmaps to identify the patient's joint positions during exercises.

The proper prediction of the patient's joints is made possible by iteratively training the Convolutional Neural Network on large scale musculoskeletal datasets, enabling the application to use joint recognition to offer corrective guidance in relation to the prescribed physical therapy exercise.

Alternately or in combination, joints or other patient regions are identified using position specific labels attached to a patient or user, or broadcast signals transmitted from an orthobiologic insert. Some deep learning models are validated by singularly or iteratively comparing and optimizing or improving their accuracy in predicting anatomical landmarks against annotated reference data. As a user performs each prescribed exercise, she or he is in some cases able to see his or her own kinematic model with anatomical landmarks on their mobile device screen. In some cases, a user or patient is rewarded with one or more digital badges upon completion of a prescribed repetition or exercise. Daily physical rehabilitation exercise adherence may be recorded and available for review by a treating healthcare provider, such as through their portal.

Art Therapy Software Component: Some systems comprise a pain alleviation component to provide or recommend a pain alleviation approach. Some pain alleviation approaches comprise recommending conventional pain medications, which may be administered by the patient or user or may be prescribed by a treating healthcare provider, such as through a practitioner portal.

Alternately or in combination, some systems comprise generation de novo or customization and provision of third-party generative art creation software. Some such software allows a user or patient to use their mobile device to perform a mental activity, such as coloring in or solving a visual puzzle, as may be derived from previously existent or newly created digital artwork such as may be generated daily. Before the user begins the art therapy session, they are in some cases asked to select from a collection of nonpharmaceutical pain alleviation approaches, such as whether they would prefer to color or solve a visual puzzle. Once they have made their selection, or prior to their selection, they are in some cases prompted to enter their current pain score, for example on a scale of 0 to 10 or other self-assessed or externally evaluated approach for pain assessment. Alternately, or in combination, a user or patient is asked if they would like to select music to play from the application's library of public domain or proprietary music during the session. Concurrent with or after completion of a nonpharmaceutical pain alleviation regimen, they are prompted to enter their current pain score, which is entered and may be provided on a physician's portal or other practitioner portal. In some cases, the total time of the art therapy session is recorded alongside the two pain scores in their recovery profile. Various embodiments of art therapies or other alternate pain reduction therapies exhibit a pain reduction of at least, about, or no more than 5%, 10%, 15%, 20%, 25%, 30%, 35%, 40%, 45%, 50%, 55%, 6-%, 65%, 705, 75% 80%, 85%, 90%, 90%, or up to 100%.

Pose-estimation and Art Therapy Component Synergy. Software components in some cases allow for a synergistic intertwining of data collected and processed from the Pose-Estimation and Art Therapy components into a composite assessment. A composite assessment may allow a user or medical practitioner to extrapolate insights that consider both physical therapy adherence and Art Therapy adherence for individual pain improvement. The composite assessment may enable the software application to recommend alternative Art Therapy pathways, such as in the case that physical therapy adherence has been confirmed by the software without an improvement in the pain score over a set period, such as over a number of sessions or a period of time, for example, 1, 2, 3, 4 5, 6, or 7 or more days, or 1, 2, 3, 4 or more than 4 weeks, 1, 2 or more than 2 months, for example over two week intervals. Users are in some cases also provided with a comparative score of their Physical Therapy adherence in relation to their Art Therapy adherence.

Physician Portal Software Component: A physician's or practitioner's portal facilitates communication, evaluation of or oversight of a user's or patient's rehabilitation or therapeutic regimen. Various portals allow a practitioner to monitor and chart the patient's daily pain score, physical rehabilitation, and art therapy adherence, add additional data such as comorbidities and body mass index scores. The portal is accessible, such as through the web and is often navigable on a desktop or mobile device. The portal also gives a practitioner the ability to view which CPT (Current Procedural Terminology) codes they are eligible to be reimbursed for by monitoring the patient's remote physical rehabilitation, pain score progress, and art therapy sessions. The portal may also include an option to send an asynchronous text or video message to the patient's inbox or to call them on their phone number.

Sensor components. Some kits further comprise sensor components, such as components indicative of user posture, position, movement, joint or other body part location. Some sensors indicate orthobiologic location. Sensors may be attached to the user, worn by the user, for example at joints or positions indicative of joint location, or integrated into a carried or worn user device such as a phone or watch. Some systems employ a plurality of sensors, such as in joint proximity, while other systems rely upon a single sensor such as a watch or carried phone, while other systems derive joint or user posture information from an image, images, or a recording of patient movement pursuant to executing a regimen constituent movement or movements.

Movement-Pain Evaluation

System components such as those above facilitate practice of a broad range of methods relating to movement evaluation, alone or in combination with pain alleviation through medicinal or nonmedicinal approaches.

Evaluating mobility and addressing mobility associated pain. A common theme of a plurality of such methods relates to mobility evaluation, often in combination with addressing mobility associated pain. Various embodiments relate to applying such methods to evaluation of mobility impairment and associated pain in the context of patient evaluation pursuant to surgery selection, identification of a joint or region for a surgical intervention such as an intervention comprising delivery of an orthobiologic component, or for a nonsurgical intervention regimen.

Alternately, some embodiments relate to mobility performance rather than mobility impairment, as in the case of practice of the methods and use of systems herein by an athlete to assess performance of an athletic task. In some such cases, pain evaluation is replaced by difficulty assessment or fatigue assessment.

Practice of these methods variously comprises one or more of capturing motion information from a user, tagging the information such that it may be stored for temporal comparison or correlated with the user or patient, in particular the intervention or orthobiologic introduced into the patient or user. Motion may be captured through use of a video recording device such as a handheld mobile device, through use of a carried or attached movement detector, alone or in combination with position or joint indicative markers that may be worn or attached to positions on a user or patient.

A motion capture video, such as generated by a depth sense camera, or dataset is compared to a reference so as to evaluate mobility performance. The performance is variously performance of a routine task such as walking or an untargeted measurement of motion throughout a period of time. Alternately, in some cases data is captured pursuant to patient performance of one or more physical therapy or mobility evaluation exercises or activities, such as physical therapy or mobility exercise or activities prescribed either for mobility evaluation or for mobility improvement, such as pursuant to physical therapy.

A number of references are consistent with various embodiments of the technology herein. Exemplary references include a dataset generated from at least one prior performance of the evaluation exercise or activity by the user or patient, such as before an intervention or subsequent to an intervention, or an idealized or healthy performance of the evaluation exercise or activity.

Some methods comprise data preprocessing to filter noise before the software applies computer vision algorithms to analyze the video frames of the patient, such as in real time, to assess user or patient pose. Pose estimation in some cases comprises identification of key anatomical landmarks such as joints.

Some methods comprise using an a priori algorithm, while alternatives are trained on datasets, such as large, annotated datasets. Exemplary methods detect a patient's joints through the use of deep learning models developed using a deep learning library such as the Pytorch machine learning library. Alternately or in combination, joints or other patient regions are identified using position specific labels attached to a patient or user, or broadcast signals transmitted from an orthobiologic insert. Some deep learning models are validated by singularly or iteratively comparing and optimizing or improving their accuracy in predicting anatomical landmarks against annotated reference data. As a user performs each prescribed exercise, she or he is able to see his or her own kinematic model with anatomical landmarks on their mobile device screen.

In some cases, a user or patient is rewarded with one or more digital badges or other indicators of task completion upon completion of a prescribed repetition or exercise. Daily physical rehabilitation exercise adherence may be recorded and available for review by a treating healthcare provider, such as through their portal.

Rehabilitation progression gating. Some methods further relate to prescribing a gated change in a rehabilitation regimen task in response to completion of a prescribed repetition or exercise. Completion is assessed in light of performance of a particular exercise task, performance of a particular exercise task at above a threshold of similarity to a reference such as an a priori reference or other reference contemplated herein or elsewhere, performance of a particular exercise task at a self-reported pain level below a threshold, or both above a threshold of similarity to a reference and below a self-reported pain level threshold.

Gated changes in a rehabilitation regimen often comprises providing a change in rehabilitation regimen or progression through a rehabilitation regimen in response to evaluated performance. The regimen is often selected by a medical practitioner, and progression through gated steps in the regimen is often confirmed or approved by a medical practitioner prior to being provided to the user. A benefit of the systems and methods herein is that a preliminary or dispositive assessment of user performance is provided to the medical professional, such that the medical professional does not need to observe individual performance of particular exercises by the user. Rather, the systems or methods provide a performance assessment to the medical practitioner, in some cases accompanied by video or still images relevant to or informative of performance, such that the medical practitioner may assess performance, alone or in combination with patient pain self-assessment.

Progression is in some cases linear, in that a user either progresses or does not progress from a first exercise to a second exercise in light of an exercise evaluation, alone or in combination with a self-reported pain assessment. The exercise evaluation is performed either by a system herein or by a medical professional to which performance results or performance results and pain self-reporting is reported or images or video information provided.

Alternately, progression is in some cases bifurcated or branched, such that a second exercise is selected from a plurality of second sexercise alternatives in light of an exercise evaluation, alone or in combination with a self-reported pain assessment. The exercise evaluation is performed either by a system herein or by a medical professional to which performance results or performance results and pain self-reporting is reported or images or video information provided.

Self-reported pain assessment is evaluated in some cases in light of reported pain level prior to exercise performance, reported level subsequent to exercise performance, reported level subsequent to performance of a system-provided alternative pain amelioration activity such as art therapy, for example a mental activity such as coloring in or solving a visual puzzle, or even degree of change in self-reported pain level between any of the reporting checkpoints mentioned above such as prior to exercise, subsequent to exercise or subsequent to a pain amelioration activity. That is, exercise regimen progression may be gated by any one or more of system evaluation or medical practitioner evaluation of exercise performance, self-reported pain level, or change in self-reported pain level pursuant to an exercise execution.

Progression may comprise selecting or proposing, autonomously or resulting from providing results to a medical professional, escalation of difficulty of an exercise, progression to a second exercise, ceasing or reducing difficulty of an exercise, isolating or removing a particular component or movement in an exercise, alternating among exercises or between a first exercise and a second exercise, or completion of an exercise regimen. Exercise progression may comprise proceeding through a set of exercises focusing on a particular orthobiologic component or intervention relating to a particular orthobiologic component, alone or in combination with orthobiologic component-independent exercises.

Compliance incentivization. Systems and methods herein may in some cases track performance of an exercise or a progression among a plurality of exercise in an exercise or rehabilitation regimen. Performance is in some cases tracked as completion of a first exercise in an exercise regimen. Alternately or in combination, performance is evaluated as degree of compliance to or conformation to a target or model reference data set such as a set contemplated herein.

Progression is in some cases reported to a medical professional. Alternately or in combination, performance is reported to the user. The user may variously access any one or more of exercise completion, degree of compliance to or conformation to a target or model reference data, change in compliance to a target or model, and self-reported pain level at any one or more of a set of pain reporting checkpoints.

Physical rehabilitation is in some cases difficult for a user to comply with because progression is not readily apparent. Patients may lose incentive to comply to a rehabilitation regimen because of a lack of awareness of or sense of accomplishment or failure to feel as if progress is occurring, or because of a feeling that progress has either plateaued or completed. By providing compliance data, particularly in the form of changes in degree of compliance to or conformation to a target or model reference data set, change in compliance to a target or model, and self-reported pain level at any one or more of a set of pain reporting checkpoints, a user may be able to visualize progression through a rehabilitation regimen so as to be incentivized to continue along the regimen even if the user does not feel or is not otherwise aware of progress or improvement.

That is, systems and methods herein enable a user to concurrently document movement improvement, such as movement improvement related to a orthobiologic insert, and pain management demand improvement. Such documentation may be provided to a user so as to incentivize compliance, for example by demonstrating progress or points of improvement to the user. Such documentation may be provided to a medical professional so as to allow assessment of a rehabilitation regimen, for example pursuant to modification of such a regimen or pursuant to assessment of the need for or efficacy of follow-on intervention. Such documentation may be provided to an orthobiologic manufacturer or provider, so as to assess efficacy of the orthobiologic, such documentation may be provided to a medical professional or an insurer, so as to assess user compliance or user need for additional surgery or pharmaceutical pain intervention.

Surgery independent movement and pain assessment. As mentioned above, systems and methods herein facilitate not only recovery from surgery, such as surgery relating to introduction of an orthobiologic, but also surgery-independent movement, alone or integrated with movement related pain assessment and alleviation, in some cases in a system to facilitate reporting to a medical provider such as a remote medical provider or other movement assessor, or to document movement for ongoing assessment.

That is, the systems and methods herein are in some cases used to assess movement or movement and self-reported pain in the contest of surgical assessment. A user may, for example, have suffered an acute event such as a fall, car accident or other skeletal or neurological trauma, or example, such that movement is impaired. Alternately, a user may suffer from a chronic or ongoing issue such as a herniated disk, spina bifida, multiple sclerosis or other disorder impacting movement.

Systems and methods herein facilitate movement assessment, alone or in combination with pain assessment, so as to facilitate degree of movement impact, either at a particular point or over time. Assessment may be done so as to compare a movement data set for an individual to either a healthy movement dataset, for example so as to detect deviation from a healthy movement dataset consistent with a particular disorder, such as loss of mobility at a particular disk or vertebra. Alternately or in combination, one may compare to one or more datasets consistent with particular disorders, such that alignment with a dataset indicates presence of the disorder associated with the dataset. Concurrently, self-reported pain assessment may indicate severity of impact on user quality of life, and efficacy of nonmedicinal pain management to reduce self-reported pain levels may indicate the viability or likelihood of completion of a rehabilitation regimen.

Such an assessment may comprise or facilitate one or more of the following: rehabilitation selection, injury identification, orthobiologic identification, or surgery selection. Such assessment may comprise an individual assessment data set collection, or may comprise a temporal series of data collection events, so as to assess user progression over time. In some such cases, trends in performance over time such as one or more of decreasing deviation from healthy dataset positioning, increasing deviation from injury or disorder dataset positioning, improvement relative to original movement dataset, decrease in self-reported pain level, increase in responsiveness to alternative pain mediation may be assessed to provide patient condition or select a future course of action. Assessment is in some cases made by a medical practitioner to whom the dataset or datasets are reported, for example through a remote terminal functionality provided pursuant to a system herein. Alternately or in combination, assessment is made through artificial intelligence or other automated or computer or cloud-based data assessment.

Movement assessment may be performed independent of injury or surgical intervention. For example, an athletic performance dataset comprising one or a temporal series of movement performances may be collected. This data may be compared to a dataset or datasets associated with model or correct movement, or with incorrect movement, or both correct and incorrect movement, so as to assess user technique or form in performing a motion, risk of injury in performing the motion, or change in the motion in response to coaching or practice. Exemplary motions in these embodiments include pitching, such as pitching that may imperil elbow health or performed subsequent to elbow surgery, basketball free-throw or other shot taking, other throwing, golf ball or tennis ball striking or other activity comprising or involving spinal movement, balance exercises such as gymnastic performance, running such as sprinting or distance running, other track and field event performance, skiing, swimming or diving, or other sport or physical activity, performed by a professional or amateur.

Assessment of sport or other physical performance in some cases further comprises a self-reported pain assessment or in some cases a self-reported fatigue assessment, alone or made before and after a post-performance treatment such as icing, massage, or nonmedicinal pain management.

Data collected from such an assessment may be presented to a user, and or may be provided to a medical practitioner or athletic specialist such as a coach or trainer who may be remote to the user.

Data collection. A number of data collection approaches are consistent with the disclosure herein. Data are in some cases collected through a single data collection system such as a video recorder as is found in a handheld device. Alternate data collection systems further comprise markers such as joint markers to identify particular joints or portions of a user body or indicative of position or motion of the user.

Substantial data processing may be performed so as to identify particular joints or movements pursuant to user performance of an activity. Processing may comprise identifying joint position and joint movement pursuant to performance of a movement or series of movements. Identification may be aided by joint markers, or may be performed solely on a video or image of user movement.

Data presentation. Data may be presented across a spectrum of approaches.

A most direct data presentation approach comprises delivering positive or negative outcomes, such as 'check' or 'x' for performance within a threshold deviation from a target, at a level of improvement, or outside of a threshold for a negative movement model. Such a system facilitates visualization of multiple measurement sessions or instances over time, such that a user or medical professional may observe successful compliance over time through multiple steps of a treatment regimen. The output may additionally be modified or multiply depicted to indicate pain level at one or more pain level assessment points. That is, a check for successful performance may be colored or bolded, for example to indicate self-reported pain level prior to, immediately after or subsequent to nonmedicinal pain intervention following performance of an instance of movement monitoring, or change in pain level following nonmedicinal pain management. Output may be additionally modified so as to incentivize compliance or continued performance, for example by indicating a duration of consecutive performance (a 'streak'), or a duration at a particular pain level or attainment of a new pain level or progression through a gating to a new exercise in an exercise or therapy regimen.

More data rich presentation methods may also be used, particularly in presentation of movement data to a medical practitioner. For example, data may depict a value representative of deviation from a reference, such as a healthy movement pattern, an injured or affected movement pattern, or a previous movement pattern data set of the user.

The data may further indicate which joints or which components of the movement pattern contribute to deviation, if any, from a model or reference data set. Some datasets may further depict or allow a user or a medical practitioner to select or observe a stored user movement video corresponding to a dataset or dataset component. In yet further embodiments, depictions corresponding to user joint or other body positions are highlighted or otherwise marked to indicate where in the completion of a movement or exercise the joint or body part deviates from a reference, such as a healthy movement pattern, an injured or affected movement pattern, or a previous movement pattern data set of the user.

Pain Medication Reduction

Nonmedicinal pain reduction. Systems and methods herein relate to replacement of medicinal pain treatment using nonmedical pain amelioration or reduction approaches. Some systems comprise providing mental stimulation or mental distraction as an approach to pain reduction. Such mental stimulation may be effected through generation de novo or customization and provision of third-party generative art creation software or art or other puzzle activities, for example so as to engage a user mentally or otherwise distract a user from pain such as post movement pain.

Examples include drawing or coloring exercises, art-related puzzles, memorization exercises, mathematical puzzles, presenting optical illusion visual puzzles, music, text such as poetry or riddles, or other distracting or engaging subject matter.

Nonmedical pain reduction is provided in response to movement or regimen portion completion followed by self-reported pain, in some cases above a threshold or alternately whenever such pain is present. In some cases, the complexity, elaborateness, volume, duration or other parameter of the nonmedical pain reduction is tailored to the magnitude of the self-reported pain. Alternately, pain reduction is provided in response to self-reported pain independent of the level reported.

Nonmedical pain reduction is provided alone or in combination with medicinal pain reduction in various embodiments. In some cases, efficacy of nonmedical pain reduction indicates a reduced need for medical pain reduction, such that medical pain reduction may be reduced or prescribed at a lower level in response to observation of efficacy of nonmedical pain reduction as measured for example by reduction in self-reported pain following nonmedical pain reduction therapy.

Various embodiments of art therapies or other alternate pain reduction therapies exhibit a pain reduction of at least, about, or no more than 5%, 10%, 15%, 20%, 25%, 30%, 35%, 40%, 45%, 50%, 55%, 6-%, 65%, 705, 75% 80%, 85%, 90%, 90%, or up to 100%, as measured by self-reported pain levels before and after an individual pain reduction therapy instance.

Similarly, various embodiments of art therapies or other alternate pain reduction therapies result in a reduction of use in medicinal pain reduction of at least, about, or no more than 5%, 10%, 15%, 20%, 25%, 30%, 35%, 40%, 45%, 50%, 55%, 6-%, 65%, 705, 75% 80%, 85%, 90%, 90%, or up to 100%, relative to a control individual or set of individuals undergoing a comparable regimen not using a method or system herein.

The accessibility of alternate pain reduction immediately after motion or exercise completion or cessation may reduce the time during which a user may experience post-exercise pain. Accordingly, practice of alternate pain reduction herein may reduce the overall pain associated with movement or exercise, so as to increase the chance of user compliance with a therapy regimen by, for example, 10%, 20%, 30%, 40%, 50%, 60%, 70%, 80%, 90%, or 100%. Practice of alternate pain reduction herein may increase the chance of user completion of a therapy regimen by, for example, 10%, 20%, 30%, 40%, 50%, 60%, 70%, 80%, 90%, or 100%. Practice of alternate pain reduction herein may increase user progress through a regimen at a set time period (for example, 1, 2, 3, 4, 5, 6, 7, 8 weeks, 3, 4, 5, 6, months or more) after initiating a therapy regimen by, for example, 10%, 20%, 30%, 40%, 50%, 60%, 70%, 80%, 90%, or 100% or more. Practice of alternate pain reduction herein may increase user recovery at a set time period (for example, 1, 2, 3, 4, 5, 6, 7, 8 weeks, 3, 4, 5, 6, months or more) after initiating a therapy regimen by, for example, 10%, 20%, 30%, 40%, 50%, 60%, 70%, 80%, 90%, or 100% or more. All measurements are variously relative to a control individual or set of individuals undergoing a comparable regimen not using an alternate pain reduction herein.

Informing gated regimen progression. Upon completion of a nonmedical pain reduction exercise, user pain level may be again self-reported so as to again measure pain levels. Levels or changes in self-reported pain levels may inform the level of stress the movement exercise placed on the user, and may inform progression through a gated therapeutic movement regimen, or selection of which from a plurality of options for progression. Progression decisions are in some cases made through artificial intelligence or other automated analysis through systems herein. Alternately, decisions are made by a medical professional to whom results are reported, such as remotely, alone or informed by recommendations provided through artificial intelligence or other automated analysis. Progression decisions variously comprise gating advancement through a linear course, selecting among a first and a second option for progression through a bifurcated course, decisions to remain at a current stage of a regimen because of pain levels independent of user movement data positive or negative correlation to a reference model, increasing or decreasing rest intervals between movement exercises, or other moderation or modulation of regimen progression.

Monitoring of self-reporting. Through systems and methods herein, user pain self-reporting is monitored, such as prior to movement recordation, subsequent to movement recordation, and subsequent to undergoing nonmedical pain reduction. Pain levels may be analyzed, such as through automated or AI driven analysis, and trends reported to the user or to a healthcare practitioner, such as a remote healthcare practitioner.

Data may be analyzed for trends between movement recording sessions or among reportings related to a single movement session or both between sessions and among reportings as part of a single session. Analysis outcomes variously comprise informing gating regimen progression, informing medicinal pain reduction selection or dosage, informing nonmedical pain reduction exercise selection or duration, or informing decisions related to surgical progression or orthobiologic selection of surgical progression is selected.

Action thresholds. In various embodiments, a pain gated action threshold is passed if a pre-exercise self-reported pain level remains at 95%, 90%, 80%, 70%, 60%, 50%, for example, of a prior self-reported pain level or of a maximum pain level for 1, 2, 3, 4, 5, 6, 7, 8, 9, 10 or more than 10 exercise or movement sessions. Similarly, in various embodiments, a pain gated action threshold is passed if a post-exercise self-reported pain level remains at 95%, 90%, 80%, 70%, 60%, 50%, for example, of prior self-reported pain level or of a maximum pain level for 1, 2, 3, 4, 5, 6, 7, 8, 9, 10 or more than 10 exercise or movement sessions, or 100%, 110%, 120%, 130%, 140%, 150% or greater than 150% of a pre-exercise self-reported pain level for a given session. Similarly, in various embodiments, a pain gated action threshold is passed if a post-nommedical pain reduction exercise self-reported pain level remains at 95%, 90%, 80%, 70%, 60%, 50%, for example, or prior self-reported pain level or of a maximum pain level for 1, 2, 3, 4, 5, 6, 7, 8, 9, 10 or more than 10 exercise or movement sessions, or remains at 95%, 90%, 80%, 70%, 60%, 50%, for example, of a pre-exercise or post-exercise self-reported pain level for a given exercise or movement instance. Action thresholds may inform gating regimen progression, informing medicinal pain reduction selection or dosage, informing nonmedical pain reduction exercise selection or duration, or informing decisions related to surgical progression or orthobiologic selection of surgical progression is selected.

Synergy of Pose Estimation and Art Therapy

Some methods herein comprise a component of synergistic intertwining of data collected and processed from the Pose-Estimation and Art Therapy components into a composite assessment, which may be used to extrapolate insights that consider both physical therapy adherence and Art Therapy adherence for individual pain improvement.

The composite assessment enables the software application to recommend alternative Art Therapy pathways in the case that physical therapy adherence has been confirmed by the software or by a medical professional without an improvement in the pain score over a set period, such as over a number of sessions or a period of time, for example, 1, 2, 3, 4 5, 6, or 7, or more days, or 1, 2, 3, 4 or more than 4 weeks, 1, 2, or more than 2 months, for example over two week intervals.

Similarly, the composite assessment enables the software application to recommend alternative Physical Therapy regimen session pathways in the case that pain therapy adherence or progress has been confirmed by the software or by a medical professional without an improvement in the physical therapy session performance over a set period, such as over a number of sessions or a period of time, for example, 1, 2, 3, 4 5, 6, or 7 or more days, or 1, 2, 3, 4 or more than 4 weeks, 1, 2, or more than 2 months, for example over two week intervals.

Similarly, the composite assessment enables the software application to recommend concurrent alternative Physical Therapy regimen session pathways and alternative Pain remediation pathways in the case of system confirmed or system identified and medical professional confirmed lack of improvement in either physical therapy performance or pain remediation or both.

Patients may also be provided with a comparative score of their Physical Therapy adherence in relation to their Art Therapy adherence.

User and Medical Practitioner Reporting

Systems and methods herein have a broad range of functionalities. In addition to measuring and documenting user movement and evaluating movement relative to a reference, and documenting, ameliorating and analyzing self-reported pain levels, and in some cases analyzing user data to make recommendations, some systems and methods may present, analyze and facilitate analysis of movement or exercise data by a user or medical practitioner, such as a remote medical practitioner, such that system analyses and decisions or recommendations may be independently assessed. Similarly, some systems comprise a functionality such as an application to allow medical practitioner to remotely access user data.

Consistent with these functionalities, some systems comprise an interface or interfaces, for example for a user, a medical practitioner, or both a user and a medical practitioner may access system or method data. Such interface or interfaces are in some cases remote monitors or application or computer functionalities to facilitate data access, such as real time access or temporally remote access to user data.

Thus, systems and methods herein facilitate remote assessment by a medical practitioner, such that the medical practitioner does not need to be physically present at user movement performance or exercise completion, or the user does not need to be present at a medical practitioner office during at user movement performance or exercise completion. Images or videos are nonetheless captured and available for the medical practitioner, and accompanying data analysis and movement evaluation can be accessed, without a medical practitioner being present during user movement performance or exercise completion.

Furthermore, some systems and methods propose courses of action, such as user progression through to a next stage of a movement regimen, selection among at least one of a plurality of second stages of a movement regimen, such as in response to one or more of user movement performance relative to a reference, self-reported pain evaluation, or self-reported pain response to nonmedical or medical treatment, or other inputs, or selection of pain alleviation approaches. These courses of action are in some cases proposed independently of a medical practitioner, or serve as a gating of progression through a computationally composed or medical practitioner developed movement or movement and pain modulation regimen, or are proposed for approval or assessment by a medical practitioner who makes a final assessment as to gating or progression decisions. Often, in combination, systems and methods provide a medical practitioner with user data, such as movement reference matching or divergence data, information as to which joints or other body parts or movements result in divergence from a reference movement data set, relation of patient movement to orthobiologic insert position and movement predictions, user movement movies, user self-reported pain assessment prior to or subsequent to movement performance, or prior to and subsequent to pain intervention such as medicinal or nonmedicinal pain intervention. This information facilitates medical practitioner assessment of user performance and of system automated recommendations as to movement regimen progression.

Consequently, regimen progression recommendations are made rapidly, in some cases immediately after user movement completion of pain alleviation completion, or more rapidly or more accurately by a medical practitioner than in the absence of such systems and methods.

Thus, a user may practice or execute a movement performance or exercise without needing to schedule or be in the presence of a medical practitioner, while nonetheless not losing the benefit of the information being available to the medical practitioner, and while also gaining the benefit of automated or AI analysis of movement performance or exercise completion, sometimes in real time, and rapid assessment and regimen progression recommendations.

This rapid, convenient integration of information and recommendations has a huge effect on user compliance with a rehabilitation or other physical therapy regimen. A user may perform movement or exercise tasks at her or his convenience rather than scheduling and in some cases traveling to a remote site. Results are immediately accessible to the user and in a format that is easily assessable or digestible by the user, while at the same time being available to a medical practitioner. Nonmedicinal pain reduction is available immediately after movement or exercise completion, without prescription or delay, as is analysis of pain status or efficacy of both the exercise regimen and the nonmedicinal pain reduction approach. At the same time, information and gated progression recommendations are available to a medical practitioner, such as a remote medical practitioner, to facilitate rapid analysis of user performance and approval of user progression through a rehabilitation or other exercise regimen, including both direct progression and user performance specific modification of either movement or exercise progression, pain treatment approach, or both movement and pain approaches.

This ease of access and performance of movement exercises interacts synergistically with the ease of presentation of user progress, both in movement and in pain reduction, in providing pain amelioration, and in the recordation of 'streaks' and other progress benchmarks, so as to incentivize user compliance and ultimately user recovery.

Accordingly, practice of a method or use of a system herein may increase the chance of user compliance with a therapy regimen by, for example, 10%, 20%, 30%, 40%, 50%, 60%, 70%, 80%, 90%, or 100%. Practice of a method or use of a system herein may increase the chance of user completion of a therapy regimen by, for example, 10%, 20%, 30%, 40%, 50%, 60%, 70%, 80%, 90%, or 100%. Practice of a method or use of a system herein may increase user progress through a regimen at a set time period (for example, 1, 2, 3, 4, 5, 6, 7, 8 weeks, 3, 4, 5, 6, months or more) after initiating a therapy regimen by, for example, 10%, 20%, 30%, 40%, 50%, 60%, 70%, 80%, 90%, or 100% or more. Practice of a method or use of a system herein may increase user recovery at a set time period (for example, 1, 2, 3, 4, 5, 6, 7, 8 weeks, 3, 4, 5, 6, months or more) after initiating a therapy regimen by, for example, 10%, 20%, 30%, 40%, 50%, 60%, 70%, 80%, 90%, or 100% or more. All measurements are variously relative to a control individual or set of individuals undergoing a comparable regimen not using a method or system herein.

As used herein, the term "about" in the context of a number refers to a range spanning from 10% less than to 10% greater than that number, while in the context of a range refers to a larger range spanning from 10% below the lower listed limit to 10% greater than the upper listed limit of the range.

Turning to the Figures, one sees the following.

At FIG. 1, one sees a drawing of an orthobiologic material consistent with the disclosure herein. The orthobiologic material is being twisted to demonstrate its strength and flexibility. The material is wetted with bone marrow aspirate. The combination of resilience and cell absorbency is attributable to the composition of embedded granules, bioactivated silica and the collagen matrix in which they reside. The orthobiologic is assigned an identifying or unique mobile activation code that enrolls the patient or user in a convolutional neural network-powered physical therapy program after surgery, allowing for a link from surgery to post-operative recovery and art-centered pain management.

Figure 2:
FIG. 2 shows a user performing a prescribed physical therapy exercise while a convolutional neural network extrapolates the user's joint positions pursuant to assessing proper exercise performance.

At FIG. 2, one sees a user performing a prescribed physical therapy exercise as prompted by the mobile application. The convolutional neural network underpinning the mobile application is extrapolating the user's joint positions, indicated by the darkened circles and lines, so as to assess user performance of the exercise in real time, and to record completion of an exercise. The mobile application then is able in some cases to recommend a subsequent course of progression through a multistep exercise regimen.

Figure 3:
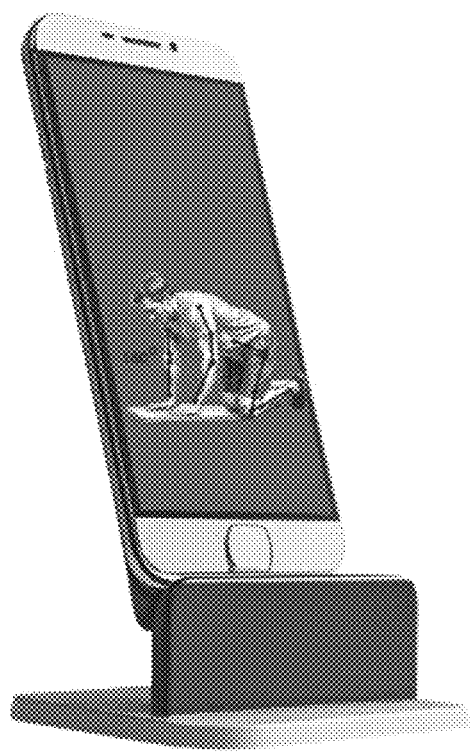
FIG. 3 shows a mobile device presenting physical therapy adherence and accuracy of performance over time.

At FIG. 3, one sees a mobile device consistent with the disclosure herein. The device in some cases captures images or a movie of the user performing the exercise regimen, and assesses performance. Physical therapy adherence and progress is visible on the user's mobile device. The user is able to see her or his own performance, and divergence or discrepancies between user performance and model performance are highlighted in real time. This allows the user to adjust performance during an exercise session rather than upon receiving feedback subsequent to performance. The performance of each individual exercise repetition, as well as the number of exercises performed, and the degree of divergence from a model are recorded and the data made available to the user and to a medical practitioner for evaluation. Upon completion of an exercise, recommendations as to progression through an exercise regimen are made to the user or for approval by a medical practitioner having access to the data.

Figure 4:
FIG. 4 shows a medical practitioner accessing a patient's physical therapy and art therapy adherence from a remote portal.

At FIG. 4, one sees that a medical practitioner can access the user's physical therapy and art therapy adherence information, both for a particular exercise and for a course of exercises over time. The data is accessed using a secure portal that includes data such as graphs of progress, a therapy regimen multi-exercise course based upon the orthobiologic lot number, with proposed next step exercises. The secure portal allows the medical practitioner to access user performance data in real time or subsequent to user performance, remote from the site of user exercise performance, such that the user does not need to schedule a medical practitioner or travel to a medical practitioner site to perform an exercise. Similarly, the medical practitioner does not need to physically observe the user in order to assess user performance or deviation from a healthy or successful performance of an exercise. Rather, the medical practitioner may rely upon joint-mapped data collected and annotated by the system and presented at the portal, system assessments of user performance, or actual images of the user. Secure portals are in some cases hardware, or may be an application or applications that a medical practitioner may access on a computer or other computational device.

Figure 5:
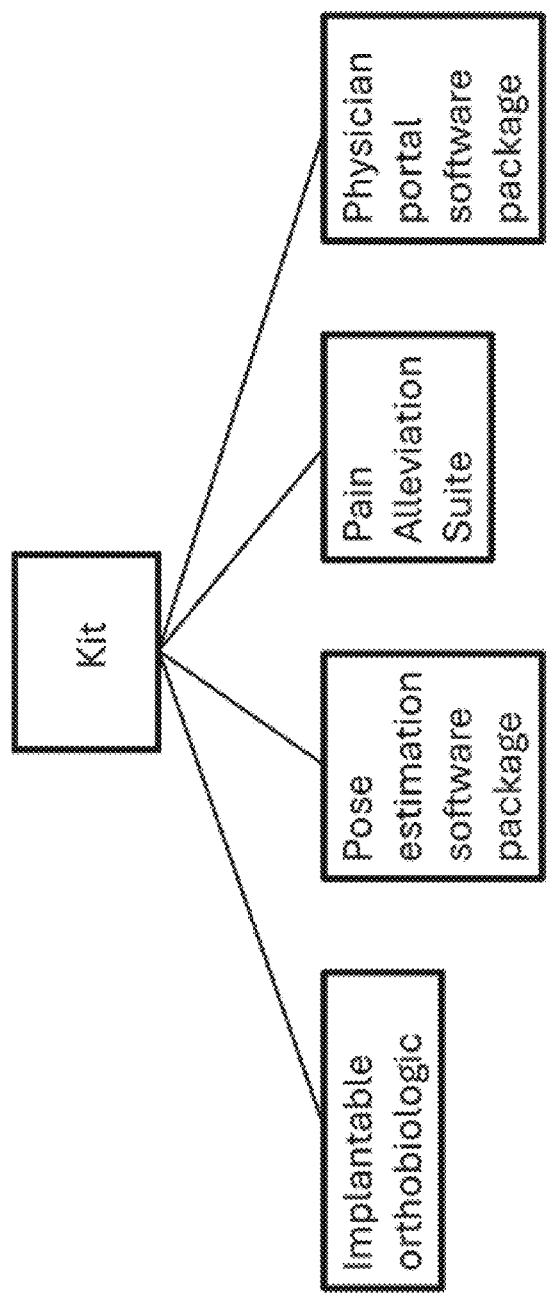
FIG. 5 shows a schematic of a kit disclosed herein, comprising an implantable orthobiologic, pose estimation software package, pain alleviation suite and physician portal software package.

At FIG. 5, one sees a kit consistent with the disclosure herein. The figure represents the implantable orthobiologic, pose estimation software package, pain alleviation suite and physician portal software packages described elsewhere herein bundled into a single kit.

Figure 6:
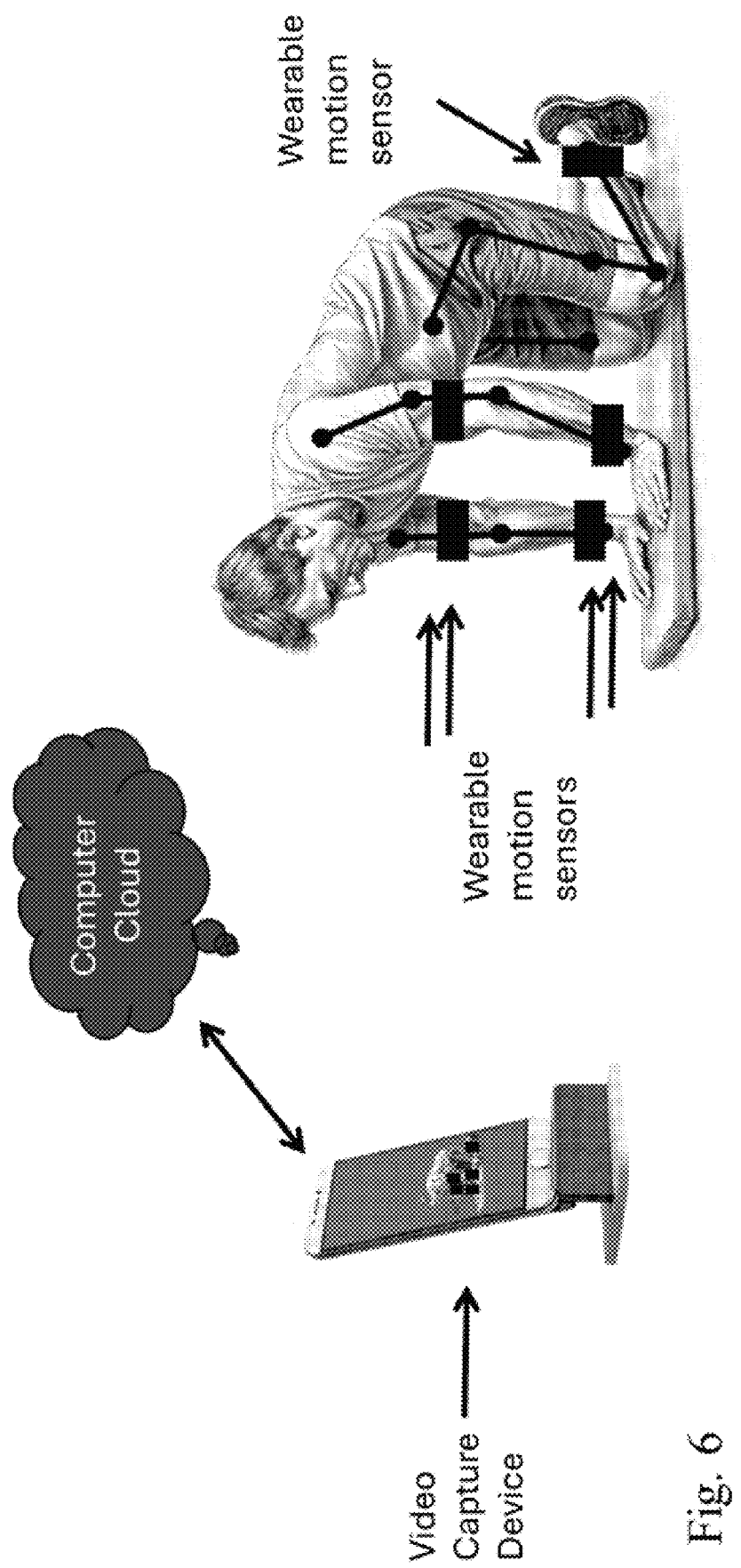
FIG. 6 shows a system disclosed herein, comprising a video capture device that captures images of an individual wearing wearable motion sensors, and that communicates the data to a computer cloud for data analysis.

At FIG. 6, one sees detection of a set of wearable motion sensors by a video capture device such as that of FIG. 3, and communication of this data to a computer cloud for cloud-based assessment.

As used herein, the term "about" in reference to a number refers to a range spanning from 10% greater to 10% less than that number, or to the nearest whole number below and above the number, whichever is greater. In reference to a range, the term refers to an extended range spanning from 10% below the lower limit to 10% above the higher limit of the listed range.

EXAMPLES

Example 1. Orthobiologic. An orthobiologic insert is synthesized for insert into a user. The orthobiologic is synthesized to have a trabecular structure similar to cancellous bone. The orthobiologic exhibits an 85% interconnected porosity among pores having a median diameter of 550 um. The orthobiologic is synthesized from a composition comprising a collagen framework and a plurality of particles. One subset of the particles comprises composite granules of 95% beta-tricalcium phosphate and 5% hydroxyapatite, a molar ratio of 61:1. Another subset of the particle comprises bioactivated glass.

The orthobiologic is delivered in hermetically-sealed packaging with a distinguishing identification code, which is printed on the package and on removable stickers. The code is used to identify the orthobiologic in a motion analysis and pain amelioration system that is provided with the orthobiologic, such that orthobiologic or the target region to which it is directed can be used to select an intervention-appropriate physical therapy regimen that is provided as a proposal to a medical practitioner.

Example 2. Orthobiologic replacement by user bone or collagen tissue. The orthobiologic of Example 1 is prepared for delivery into a user. The delivery process comprises harvesting user osteoblasts derived from a user mesenchymal stem cell population derived from bone marrow aspirate obtained concurrent with surgery, and imbibing them into the orthobiologic. As the osteoblasts are on average 20-30 um in diameter, the orthobiologic porosity allows them to both spread through and attach to the orthobiologic scaffold.

The orthobiologic is delivered to the user insertion site subsequent to imbibing, such that incorporation of user bone forming cells into orthobiologic is effected prior to delivery.

This process continues subsequent to insertion, facilitated by the orthobiologic porosity and by the granule composition. The beta-tricalcium phosphate is gradually resorbed by user tissue to be replaced by user bone or collagen formation, while the hydroxyapatite and the bioactivated glass is persistent and serves to maintain orthobiologic structure.

Example 3. Surgical intervention kit. A hospital obtains a surgical intervention kit pursuant to surgery. The kit comprises an orthobiotic insert and access to support technology. The support technology includes a rehabilitation regimen comprising multiple exercises suitable to rehabilitation subsequent to surgical insertion of the orthobiotic. The support technology also includes motion capture functionalities such that a user performing a rehabilitation regimen may be recorded and her or his performance of one or more rehabilitation routines may be captured and assessed as to its compliance to or deviation from a reference dataset. Assessment variously comprises identification of user positions such as joint positions, limb positions or posture.

Dataset references are provided by the kit, such as previously generated healthy or incrementally improved reference datasets. Alternately or in combination, references are generated through kit technology from prior user rehabilitation capture datasets.

The kit further comprises a reporting functionality, such that the user may receive a real time assessment of rehabilitation regimen performance relative to the reference, and such that a medical practitioner may also receive the assessment.

The kit further comprises a recommendation functionality, such that the kit provides a recommendation as to whether the user should continue with a current rehabilitation exercise or to progress to one or more alternate rehabilitation exercises informed by deviation from or compliance with a reference. The recommendation is submitted to the medical practitioner for independent assessment.

The kit further comprises a pain management functionality by which the user is provided with a pain management activity subsequent to performance of a rehabilitation exercise. The pain management activity may be an art project, a puzzle, or other mentally engaging activity that may redirect the user's attention from pain, such as pain associated with the rehabilitation exercise, with the surgical intervention, or with the issue necessitating the surgical intervention.

The kit comprises an interface so that it may receive a user first pain self assessment prior to performance of the pain management activity and a second pain self assessment subsequent to performance of the pain management activity. In some cases the user first pain assessment, second pain assessment or both first and second pain assessment are used by the kit to inform the recommendation functionality.

The reporting functionality is also used to provide the user first pain assessment and second pain assessment to the medical practitioner, who may use it to inform rehabilitation regimen progression decisions.

The orthobiologic is introduced to the user via a surgical intervention, and is labeled so that the kit may identify the user and correlate the user to a rehabilitation regimen tailored to the orthobiologic, the issue necessitating the intervention and to the user.

The technological components of the kit are conveyed to the user via electronic communication, such that the user may communicate with the technologies of the kit, such as by sending rehabilitation exercise data to the kit and receiving rehabilitation exercise evaluation and pain management recommendations from the kit.

A communication interface is further communicated to a medical practitioner, such that the medical practitioner may receive exercise performance information, pain management information and regimen progression recommendations, and may approve or propose regimen next steps.

Example 4. A user receives access to a kit of Example 3 pursuant to a surgery introducing the orthobiologic of the kit. Access is emailed to the user, and an image capture functionality is added to the user's personal image capture device, such as a phone.

The user receives an exercise regimen proposal, and performs the exercise under the watchful eye of his phone camera. The data are transferred to the kit where user joints and body postures are identified and assessed relative to a reference.

The user is found to deviate from the reference, and the user reports a high pain level. The kit provides a pain management activity comprising a picture to be colored in. The user reports a reduced pain level subsequent to performance of the activity without pharmaceutical intervention, thus reducing the risk of pain medication addiction associated with recovery.

The kit proposes a second exercise to address defects identified in the user's performance of the first exercise and to address the user's high reported post-exercise pain level. The second exercise is communicated to a remote medical practitioner, who approves the second exercise.

The user performs the second exercise and observes an increase in performance data compliance to the healthy reference, and decreased reported pain subsequent to performance.

The kit proposes that the user return to the first exercise, which is approved by a remote medical practitioner.

The user returns to the first exercise and performs the second exercise with a lower deviation from a reference dataset and lower reported pain, which is managed by a post-exercise pain management activity.

The user them progresses through to a third exercise toward complete rehabilitation from the surgical intervention.

We claim:

1. A kit comprising
an implantable orthobiologic having an identification code;
a computer implemented pose estimation software package comprising
a pose dataset corresponding to the identification code, wherein the identification code is associated with features comprising at least one of a recovery profile of a user of the implantable orthobiologic, biochemical characteristics of the implantable orthobiologic, and diagnosis of the user,
instructions for capturing an orthobiologic user pose image, and
instructions for correlating the orthobiologic user pose image to the pose dataset;
a computer implemented pain alleviation task suite directed to alleviation of pain related to a pose of the orthobiologic user; and
a computer implemented physician portal software package.

2. The kit of claim 1, wherein the instructions for capturing the orthobiologic user pose image is configured for instructing a mobile image device to capture the orthobiologic user pose image.

3. The kit of claim 1, wherein the instructions for correlating the orthobiologic user pose image to the pose dataset comprises instructions for detection of at least one positional marker on the user.

4. The kit of claim 1, further comprising at least one positional marker configured for being positioned on the user.

5. The kit of claim 1, further comprising a receiver configured for receiving data generated by a wearable motion sensor.

6. The kit of claim 1, further comprising a wearable motion sensor.

7. The kit of claim 1, wherein the pose dataset corresponding to the identification code comprises a kinetic model for at least one rehabilitation exercise corresponding to the pose dataset corresponding to the identification code.

8. The kit of claim 1, wherein the computer implemented pose estimation software package is configured to identify at least one anatomical landmark in a user motion dataset.

9. The kit of claim 8, wherein the user motion dataset comprises at least one video frame.

10. The kit of claim 9, wherein the at least one video frame is captured by a third party video capture device.

11. The kit of claim 8, wherein the user motion dataset comprises at least one position monitor data array.

12. The kit of claim 8, wherein the computer implemented pose estimation software package is configured to identify the at least one anatomical landmark using a deep learning model.

13. The kit of claim 12, wherein the deep learning model comprises a machine learning library.

14. The kit of claim 13, wherein the machine learning library comprises a Py Torch learning library.

15. The kit of claim 12, wherein the deep learning model is validated against the pose dataset corresponding to the identification code.

16. The kit of claim 15, wherein the computer implemented pose estimation software package is configured to generate an evaluation of positional information deviation from the pose dataset corresponding to the identification code.

17. The kit of claim 16, wherein the pose dataset corresponding to the identification code represents a pose of a healthy individual.

18. The kit of claim 16, wherein the pose dataset corresponding to the identification code represents a pre-intervention pose of an individual.

19. The kit of claim 16, wherein the pose dataset corresponding to the identification code represents a pre-intervention pose of the user.

20. The kit of claim 16, wherein the computer implemented pose estimation software package is configured to direct an operating system to record completion of a rehabilitation exercise corresponding to the pose dataset corresponding to the identification code when the positional information deviation is below a threshold.

21. The kit of claim 20, wherein the computer implemented pose estimation software package is configured to direct a monitor to display the completion of the rehabilitation exercise.

22. The kit of claim 16, wherein the computer implemented physician portal software package is configured to convey the evaluation of the positional information deviation from the pose dataset corresponding to the identification code to a monitor remote from the user.

23. The kit of claim 8, wherein the computer implemented pose estimation software package is configured to display an image comprising the at least one anatomical landmark.

24. The kit of claim 1, wherein the computer implemented pose estimation software package is configured to interface with a computer cloud based assessment capacity.

25. The kit of claim 1, wherein the identification code is affixed to packaging sealing the implantable orthobiologic.

\* \* \* \* \*